United States Patent [19]

Dempster

[11] 4,432,226
[45] Feb. 21, 1984

[54] METHOD AND APPARATUS FOR MEASURING GASEOUS OXYGEN

[76] Inventor: Philip T. Dempster, 644 McCorkle Ave., St. Helena, Calif. 94574

[21] Appl. No.: 346,010

[22] Filed: Feb. 5, 1982

[51] Int. Cl.³ ............................................. G01R 33/14
[52] U.S. Cl. ..................................... 73/27 A; 324/204
[58] Field of Search ................. 73/23, 27 A; 324/204, 324/225, 245, 246; 336/84 M, 84 R

[56] References Cited

U.S. PATENT DOCUMENTS

| | | | |
|---|---|---|---|
| 2,467,211 | 4/1949 | Hornfeck | 324/204 |
| 2,689,332 | 9/1954 | Greene | 73/27 A |
| 2,944,418 | 7/1960 | Engelhardt | 73/27 A |
| 3,049,665 | 8/1962 | Hummel | 73/27 A |
| 3,389,333 | 6/1968 | Wolff et al. | 324/225 |
| 3,720,870 | 3/1973 | Sueda | 73/23 |

Primary Examiner—Stephen A. Kreitman
Attorney, Agent, or Firm—Robert B. Block

[57] ABSTRACT

An oxygen detection system including two equal and symmetrically constructed major DC magnetic circuits each having an air gap which is alternatively filled with a sample and a reference gas. A magnetic bridge arm connects the major magnetic circuits in series opposition to derive a null response when the flux carried in the magnetic circuits is equal and a component of varying flux when the sample and reference gases are interchanged to cause an unequal flux to be developed in the circuits caused by a change in the reluctance across the gaps. An encircling inductance coil senses the flux in the null bridge arm which is electronically sampled in sychronism with the sample and reference gas interchange to develop a difference signal directly derived and proportional to the difference in magnetic susceptibility of the sample and reference gases. An active magnetic shield cancels stray fields from affecting the sensor.

7 Claims, 30 Drawing Figures

DYNAMIC DIFFERENTIAL RESPONSE

VERT: 2%/DIV.
HOR: 500m sec./DIV.

REFERENCE AND SAMPLE
TUBES ARE SIMULTANEOUSLY
EXPOSED TO AN ABRUPT
CHANGE FROM NORMAL
ATMOSPHERE TO 100% O₂.
LEFT HAND OF PICTURE IS
AIR AND RIGHT HAND IS O₂

METHOD AND APPARATUS FOR MEASURING GASEOUS OXYGEN

BACKGROUND OF THE INVENTION

This invention relates to the quantitative measurement of the amount of free oxygen in a gaseous mixture of the same with other gases. The invention finds application to the measurement of the precentage of oxygen content in fuel mixtures, both before and after burning, as in measurements in industrial combustion of fuels and in internal combustion engine analyses, and finds a special application in pulmonary function testing in which the inhalation and exhalation of a patient is being monitored for oxygen uptake.

The invention is based on the difference in magnetic susceptibility of oxygen gas, O2, (which designation will be hereinafter used in place of $0_2$) relative to other gases. It is well-known that oxygen gas is highly paramagnetic compared to most other gases and has a high positive value of magnetic susceptibility. Susceptibility is usually defined either by volume or by mass (volume divided by density) and especially relates to the property of a substance, (designated herein by k) which is a measure of the intensity of the magnetization induced in a unit volume of the substance by unit of applied magnetic field. A positive value indicates that the magnetic field within the substance exceeds the magnetic field in free space. The volume susceptibility will be referred to herein for the sake of uniformity and for oxygen gas is paramagnetic, positive and of the order of $10^{-7}$.

Oxygen gas is uniquely paramagnetic compared with other common gases which are usually weakly diamagnetic. Thus, the presence of oxygen can be quantitatively determined by the use of magnetic measurements of a sample gas compared to a reference gas of known content as for example; nitrogen free of oxygen (hereinafter N2), oxygen in a pure form, or a known mixture of oxygen and gases such as ambient air.

For some time a need has existed for an instrument and system capable of accurately measuring the free gaseous oxygen content of sample gases. Such an instrument should be accurate and it should respond rapidly. Attempts to use the difference in magnetic properties of oxygen compared to other gases have been proposed and generally rely on absolute magnetic flux measurements or differences in the absolute magnetic flux which can be obtained in substituting sample and reference gas mixtures in magnetic circuits. However, the susceptibility difference in such systems amounts to such a small part of the entire measurement that the measurement technique required a remarkable insensitivity to any other factors which are present which can be at least as large or larger than the changes in oxygen content. Of these, thermal effects, slight changes of the measuring geometry caused by mechanical movements, stray electric fields and magnetic fields all cause changes in the measuring instrument which are often of a magnitude which destroy the possibility of successfully making the measurement required. While many systems have been proposed, it is not believed that any have achieved freedom from interference and sensitivity requisite of a good practical instrument.

Examples of the foregoing include U.S. Pat. No. 3,049,665 to Hummel in which a sample and reference cells enclosed within sensing coils are formed in a two-arm magnetic circuit by having a common element including a driving coil. The absolute values of the induced fields in the arms are sensed by the coils to produce electrical signals which are combined to produce a difference signal ostensibly proportional to the magnetic susceptibility of the sample and reference gases. This is in essence an electrical signal subtraction of signals derived from changes in the entire magnetic field of magnetic circuits including sample and reference gas gaps, but is found to be impractical because the thermal, mechanical, and magnetic disturbances are at least as large as the difference sought to be measured and mask the effect.

U.S. Pat. No. 2,467,211 to Hornfeck also uses absolute difference measurements in the reluctance of a flux path caused by alternating the sample and reference gases through the path. This also requires detecting changes of the order of $10^{-7}$ of the total effect measured and is subject to the same difficulties as the Hummel patent, '665.

U.S. Pat. No. 2,689,332 to Green proposes an improved structure for balancing out mechanical vibrations and would appear to be effective but nevertheless requires the measurements of the gross change in the magnetic flux caused by a change in the susceptibility of the sample in a gap. U.S. Pat. No. 3,720,870 to Swatha proposes changing the sample and reference gases through a gap in a single magnetically biased circuit and noting the changes in induced voltages in the coil due to the difference in magnitude due to susceptibility. This still requires measurement of the overall gross magnetic flux due to the first and second samples in order to obtain a difference. In sum, the references disclosed rely on the ability of a electrically connected coil to sense a change in a very large value of total flux density and thus are inherently incapable of making a direct measurement of the flux difference while excluding the presence of the gross magnetic flux from the measurement circuit and are thus subject to the common difficulty of attempting to measure in the presence of a major flux a change of extraordinarily small magnitude.

There is therefore, a need for a new and improved method and apparatus for analyzing gases for oxygen content and for determining the percentage of oxygen quantitatively.

SUMMARY OF THE INVENTION AND OBJECTS

In general, it is an object of the present invention to provide a method and apparatus for detecting gaseous oxygen which will overcome the above limitations and disadvantages.

Another object of the invention is to provide an oxygen detection system of the above character which operates on the principle of a balanced magnetic bridge in which an arm of the bridge is balanced between two magnetic circuits carrying the major flux of a sample and reference circuits, the difference in susceptibility of which is detected by an imbalance between the circuits, the imbalance being the direct flux which is measured.

A further object of the invention is to provide an oxygen detection system of the above character which is mechanically stable and thus immune in large part to detection of spurious signals created by vibration and other mechanical movements in its vicinity.

Another object of the invention is to provide an oxygen detection system of the above character which employs a balanced magnetic circuit which is highly symmetrical and therefore which is inherently immune to magnetic disturbances and stray electro-magnetic fields.

Another object of the invention is to provide an oxygen detector of the detection system of the above character which is further provided with circuits for eliminating stray electro-magnetic fields from influencing the same and which nevertheless is extremely sensitive to small changes in magnetic field strength.

Another object of the invention is to provide an oxygen detection system of the above character which is capable of giving a read-out and percentage of oxygen present in a sample gas in quatitative terms and which has a very low residual noise output.

Another object of the invention is to provide a pulmonary function and analysis system capable of real time read out of oxygen content of inhalation and exhalation.

Another object of the invention is to provide a gaseous detection system of the above character having low noise and extremely good rejection of responses to stray electro-magnetic fields.

In general the invention is achieved by employing two equal and symmetrical major magnetic circuits each having a DC magnetic source of equal value and each having an air gap which is alternatively filled with a sample and a reference gas. The reference gas may be pure oxygen or pure nitrogen for example or may be air. The difference is susceptibility of the gases will be measured and is commonly almost entirely due to the oxygen content difference of the gases. The circuits are connected in series opposition magnetically through an included magnetic bridge arm arranged for a null response when the flux carried in the major magnetic circuits is equal. When the sample and reference gases are interchanged, any difference in susceptibility will appear as a change in the reluctance across the air gaps and cause an imbalance flux to flow in the bridge arm. This imbalance flux is sensed by an inductance coil encircling the arm and is sychronously sampled with the gas flow interchange to generate difference signal between the interchange conditions. The difference signal is subtracted to give a sum signal proportional to and directly derived from the difference in susceptibility of the gases and based directly upon a magnetic comparison within the magnetic sensor described. A particularly active magnetic shield is employed in which the magnetic sensor of this invention is mounted. The magnetic shield serves to cancel out stray fields which would otherwise affect the measurement.

These and other objects and features of the invention will become apparent from the following description when taken in conjunction with the accompanying drawings of which:

BRIEF DESCRIPTION OF THE DRAWINGS

FIG. 2 is a cross-sectional view of the magnetic detection apparatus including sample and reference cells constructed in accordance with the present invention.

FIGS. 3 through 6 are detailed schematic diagrams of the electrical circuits and connections associated with the oxygen detector of FIG. 1; FIG. 3 relating to the clock and control logic; FIG. 4 relating to the signal preamplification and filtering; FIG. 5 relating to sample and hold integration and difference amplification circuits; and FIG. 6 relating to stray magnetic field sensor and eliminator.

FIGS. 8A–8F are graphs showing the performance characteristics of the oxygen detector built according to the present invention.

BRIEF DESCRIPTION OF THE PREFERRED EMBODIMENT

Figure 1:
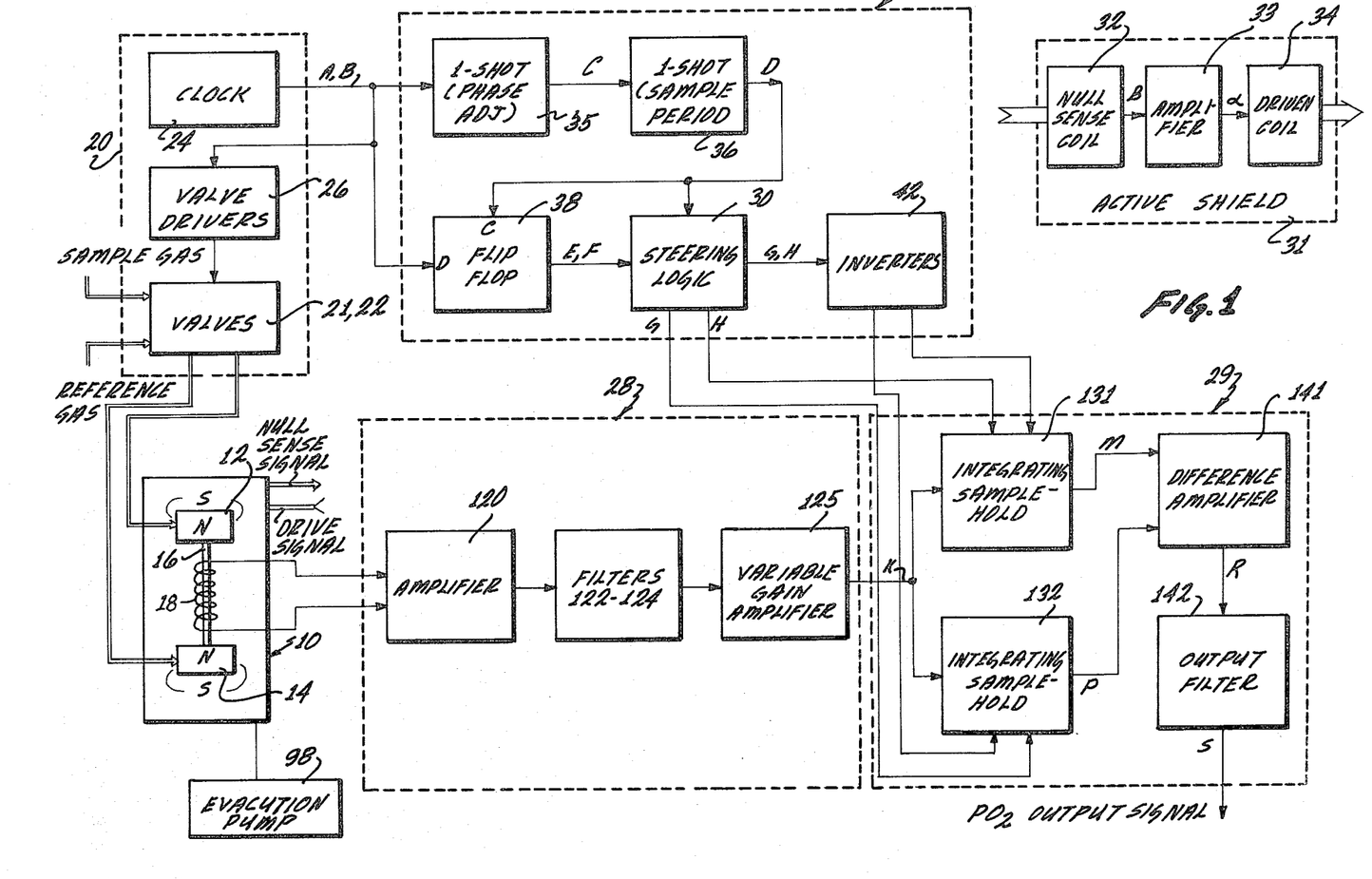
FIG. 1 is a schematic diagram of the oxygen detection system of the present invention.
Figures 2, 8F:
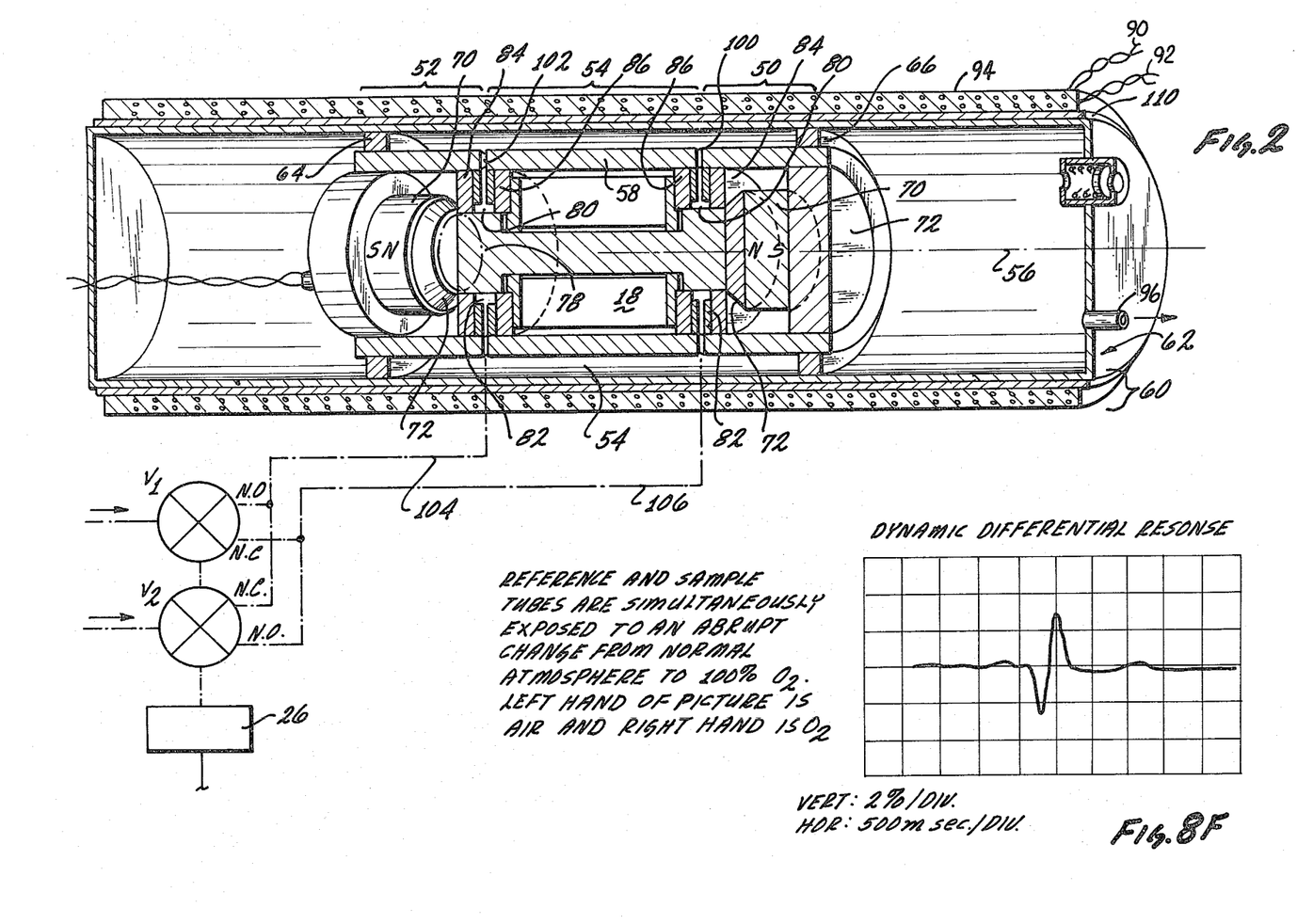

Referring now to FIG. 1 the general scheme of the oxygen measuring system of the present invention is illustrated in block and diagramatic form. Thus, a DC driven magnetic difference sensor 10 is provided which contains interchangeable sample and reference chambers 12, 14 for the sample and reference gases to be passed. Each of the chambers is arranged to form a gap in a major flux path of a circuit supplied with a steady magnetic field. As the sample and reference gas are introduced, the change in reluctance of the major flux paths due to a change in the magnetic susceptibility of the respective gas causes changes in the magnetic field associated with that path. The major flux paths are magnetically coupled through an inductance bridge arm 16 which is arranged in a null configuration, so that only the difference in reluctance caused by the changing magnetic susceptibility difference of the gases is sensed and magnetically coupled through the bridge arm. These small magnetic flux variations, in that arm, are sensed by a sensing coil 18 and coupled to a signal amplifying and detection circuit 28, 29. The exchange of sample and reference gases distribution in the magnetic difference sensor are controlled by a valve control circuit 20 driving a pair of valves 21, 22 arranged and connected as indicated in FIG. 2 so that they switch connection of a sample and reference gas sources between the two, major flux carrying arms of the magnetic sensor. The valves are suitably driven by an electronic clock 24 and valve driver 26 which is a low frequency generator divided down to provide an output preferably 10 Hz. The difference signal developed in coil 18 is amplified in signal processing unit 28, filtered to discriminate against unwanted signals and adjusted to scale before being synchronously sampled by a sample and hold integrator 29. A synchronous logic circuit 30 provides a sampling signal of a phase and duration adequate to obtain accurate information from the peaks of the signal. These are integrated by the sample and hold circuit to even out the signal in time and then apply the result to a difference amplifier to produce a signal in direct proportion to the difference in magnetic susceptibility of the gases. Inasmuch as the signal being measured is so small, it is desirable to increase its strength relative to noise as many ways as possible, some of which are relatively sophisticated and will be discussed in detail herein and which pertain to the logic of sample timing. Also, and to provide additional isolation from stray magnetic fields, an active shield 31 is employed which is provided with a sense coil which drives an amplifier 33 and a driven coil 34, the sense and driven coils being incorporated with a metal shield to form, a close coupled transformer. The active shield entirely surrounds the null, or opposing, arm 16 of the magnetic sensor so that a stray field encountering the same produces a null signal which tends to cancel it.

The general operation of the oxygen detecting system of the present invention utilizes an electronic clock logic circuit 20, the clock output of which consists of a sequence of pulses A, B which are of equal duration and switch on and off, at preferably a 10 Hz rate. These pulses directly enable valve driving amplifiers 26 and valves 21, 22 which alternately open and close the sample and reference gas streams so that the sample stream is delivered to one or the other of the magnetic circuits while the reference stream is directed to the other. These connections are reversed or interchanged at a 10 Hz rate. The same signal starts a one shot 35, the output of which is adjustable with respect to its start time to provide a phase or time of start adjustment. The length of the sampling pulse is determined by a sample period circuit 36 which is used to clock a flip-flop 38, the data input of which is connected to the output of the clock 20. Suitable steering logic 30 and inverters 42 are provided for developing the correctly phased signals for controlling the integrating sample and hold circuits 29.

Sampling logic 40 is provided for generating sampling pulses which are synchronized with the sample/reference gas valve operation. The sampling pulses control the data signal input to sample and hold (S/H) integrator 29 which provides a steady electrical output proportional to the average of the peak values of the magnetic bridge sensing coil signal. A difference amplifier 141 combines the S/H signal to obtain a signal proportional to the magnetic susceptibility difference of the gases.

Referring now to the detailed magnetic circuit of FIG. 2, portions of which are shown in isometric section, there is provided first and second major magnetic flux carrying circuits generally indicated at 50 and 52, each of which includes opposite ends of a common magnetic bridge circuit 54. As shown, the structure possesses a high degree of symmetry being constructed in coaxial symmetric form about an elongated axis 56. Further, the magnetic circuits 50, 52 are mirror images of each other about the center of the structure. As used herein left and right, sample and reference, and other terms associated with each of the magnetic circuits will seem to be completely symmetric and may be interchanged. For convenience, the left magnetic circuit 52 of the drawing will be termed reference while the right magnetic circuit 50 will be termed sample. In operation, the sample and reference circuits are alternated in function at a high speed by alternating the sample and reference gas flow to each. Accordingly, the circuit descriptions herein will be undestood to apply equally to each of the sample and reference halves of the structure and a description of the one will therefore include a description of the other so as to avoid repetition of unnecessary detail.

The magnetic structure includes a cylindrical shell 58 of high magnetically permeable material such as iron, which shell provides a magnetic flux return path for both of the major magnetic circuits 50, 52 and for the null bridge circuit 54 as will be described. In addition, the shell coaxial supports the internally mounted members of the magnetic circuits and obtains relative support from a coaxially mounted surrounding active shield 60 and sensor chamber 62 via spacer rings 64 and 66. In the form of the invention given the magnetic shield 58 and chamber 62 form a unitary, bonded structure to support all of the internal components of the sensor, the components being bonded together with a suitable agent such as epoxy cement.

Each magnetic circuit includes DC magnetic source such as a permanent magnet 70 in the form of a circular disc having north and south opposing fields located at its end faces. Each magnet is coupled to the magnetic return shell by a magnetically permeable end plate 72 to form a toroidal W-shaped structure in annular cross-section. Unless otherwise stated, the term permeable when applied to magnetic structures indicates that they are highly permeable to the flow of magnetic flux and usually are made of iron of high permeability. The permanent magnets may be of any usual type, a common one now available being made of the alloy samarium cobalt and having a high field intensity to volume/weight ratio, which keeps the bulk of the sensor acceptably low. The inside or inwardly facing end of the magnet abuts a frusto-conical, permeable field focusing disc 72 which is directed toward and closes down into one end of the bridge member 16. The bridge member is of generally dumb-bell shape having enlarged ends 78 in the form of a solid cylinder intergrally joined and continuous with the elongate center section 18 and thus to the enlarged member 78 at the other side, i.e., in the other major magnetic circuit. Each end 78 is smaller than the inner dimension of the cylindrical shell within which it is located so that a magnetic air gap 80 is formed between the shell and the end piece. This gap is closed peripherally by a manifold and field ring 82 of high permeability which is supported about its periphery by being in contact with the inside of the shell. The manifold ring is supported laterally by non-permeable guide rings 84, 86. Rings 84 are preferably made of good electrically conducting material since the induced circulating currents will oppose flux change in the magnet. However, rings 86 are preferably poor electrical conductors since any circulating currents in them would oppose flux changes in the sensing arm 16, and hence, should be minimized. Rings 84 may be made of Al or Cu, while rings 86 are preferably made of poor conductivity stainless steel.

The annular cavity or gap 80 is defined by these structures, specifically by the outer, radially facing perimeter of the ends of the magnetic bridge element and the inner perimeter of the manifold ring so that the bridge end defines a floor or inward bound of an annular gap bounded outwardly by the manifold ring which defines the ceiling of the annular gap. The volume contained within the gap is further defined by the low permeability rings which define the inner and outer lateral walls.

The flux path followed by the foregoing structure will now be traced. The flux begins in the respective magnet which is similar to a small bar magnet. It crosses and spreads out through both the dumb-bell end of the magnetic bridge and through the end disc 72 closing the sensor and passes through the outer cylindrical shell which serves as the return path and through the manifold ring and gap as described. Thus, the magnetic field is confined by the generally toroidal shape of these pieces and fringes somewhat as it passes across the gap from the manifold ring to the center bridge piece. The DC field produced in each of the major magnetic circuits would be constant and defined by the combined reluctance of the path through the several permeable pieces and the gas contained in the gap. However, when the sample and reference gases are interchanged, the permeability of the gap will vary and change due to the difference in susceptibility of the gases. In differential form, a radial section through this toroidal shape yields a magnetic circuit having a single, series air gap. As is known, the gap field strength varies directly in proportion to the reluctance of the gas within the gap which is related to the geometry, the effective length of the gap and to the susceptibility of the enclosed gas. The description of the second major magnetic flux circuit shown is the same as that given above except for substitution of mirror image parts. Accordingly, like numbers have been given.

Taken together the two magnetic circuits 50, 52 are joined and arranged in a series opposition configuration in such a manner that north pole of each resides at the respective end of the bridge arm 16. The bridge arm is ferro-magnetic and has a high permeability but is balanced by the opposed magnetic circuits to a null condition. Any difference in strength of the DC magnetic poles at each end of the bridge element will only cause a DC imbalance and will not appear across the circuit when the gases are interchanged to produce an output signal. Assuming the magnetic circuit strengths to be equal, when the permeability of the contained air gaps is equal in each of the circuits, no changes will appear if the gases are interchanged and their susceptibilties are equal. However, when their susceptibilities are unequal, the resultant permeabilities of the gaps will also be unequal causing an imbalance to develop across the bridge arm. If it is assumed that the susceptibility and permeability of the right hand gap increases due to a increase in the oxygen content with the gap while that of the left hand circuit decreases due to a reduction for example, the right side of the bridge becomes more south while the left side of the bridge becomes more north. This creates an equivalent north/south magnet in the bridge.

The resultant magnetic field surge along a length of the bridge element is sensed by the inductance coil 18 and is converted into an electrical signal which is a direct measure of the difference in susceptibility of the gases. The measurable effect is enhanced by the low permeability, high electrical conductive discs or rings 84 on each side of the respective gaps, since these rings serve as a speed-up circuit by conducting magnetically induced circular currents so as to permit the immediate collapse and rise of the magnetic fields in the bridge arm.

Means is provided for shielding the sensor from the influence of stray electro-magnetic fields and includes a driven stray field sensor and null circuit which is incorporated on a sleeve of the chamber which extends throughout the length of the sensor and substantially beyond each end. The outer shield means extends about half again the length away from end of the sensor magnetic structure. The shield comprises a helically wound sensing coil 90 and a like helically wound driven coil 92 which are incorporated in a cylindrical tube which surrounds or is built upon a mu metal cylindrical shell 94 of right circular cylindrical cross-section. These together are supported on the spacers 64, 66 from the sensor so that the entire arrangement is coaxially aligned and supported together as a unitary arrangement. Each end of the tube is closed off by an end plate to form an evacuable chamber and is connected at one end through a purge valve 96 to a suitable evacuation pump 98 for partially evacuating the same. A typical pump should be capable of drawing a small vacuum, of the order of 50-100 cc of water and at a rate something in excess of 30 cc per second. The input to the manifold gaps 80 and the output are made by tapping holes on opposite sides of the sensor, through the wall of the magnetic return cylinder and radially through the annular manifold rings. The holes are continuous. Thus, the bleed holes extend from, for example, the upper side of the respective chamber gaps through the annular ring 82 and are labeled 100 and 102 in the drawings. The input is similarly taken through the lower sides and of each of the gaps through the respective annular rings and the outer magnetic shell and these are fed through lines 104, 106 to the normally closed normally open positions of a pair of bi-directional valves 21, 22. The connections are such that the valves are positively energized in each of the directions in which they operate and connect their inputs from the respective sample and gas supply, to one or the other of the lines to the sensor. In this way, in one state of activating signals, the reference gas is fed to the left side of the sensor, for example, while the sample gas is fed to the right. On reversal of the signals, the valves reverse the connection of the sample and reference gases. The valves 21, 22 are driven by the clock valve drives 26 as herein described.

Preferably the input to the valves V1, V2 is taken from means forming a dehumidification chamber. This is particularly useful in the case where one is sampling the inhalation and exhalation from a patient where a high degree of humidity is present. Such humidity may cause condensation or other artifacts in the water vapor from water droplets forming in the detection system. Since this unacceptable, the gas must be dehumidified before being measured. One method is to pass the gas through a passage which has been cooled down to some temperature just above freezing so that the air is only capable of carrying a small amount of moisture at that temperature and condensing out the remainder of the moisture in the block. The block can be arranged so that the droplets in the gas under test and then proceed down a tube to an enlarged chamber where the velocity of the gas is reduced to the point that the droplets can fall out and be drawn off through an exhaust drain such as being tied into the pump-out line which is also attached to pump 98. The sample gas is drawn off the top from this enlarged chamber with most of the moisture removed and can then proceed on to the oxygen analyzing system. The moisture which collects at the bottom of the chamber and is removed to the pump can be taken through a relatively high pneumatic resistance and then to the scavenging pump so that a small proportion of that gas is drawn through the resistance and serves to draw moisture out of the bottom of the block. While the dehumidifier mechanism is not shown herein it is believed relatively conventional in the art to employ the same.

The following are physical dimensions of a magnetic sensor constructed in accordance with the present invention. The various gas lines are conventional 1/16" inside diameter lines. All of the parts are made of soft iron except for the coils which are multiple turns of No. 40 copper wire. The overall tube length of the outer active shield is about 6" while its diameter is about 1¼" to 1½". The stray field sense coil and driven coil are about 2000 turns. The magnetic bridge element is about ¼" in diameter, of soft iron.

Figures 3, 6:
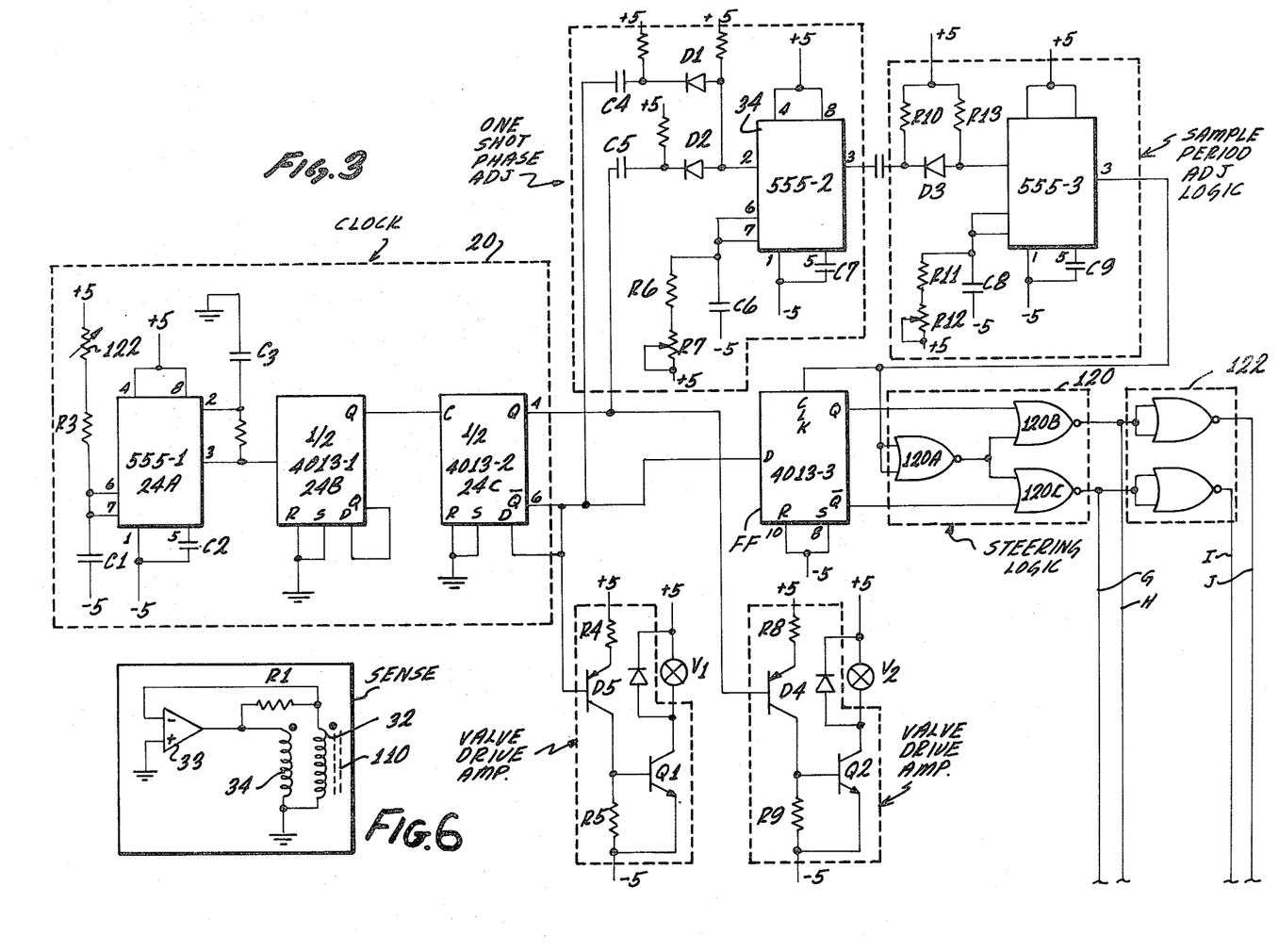

Referring now to the circuit of FIG. 6, there is shown an electrical diagram of the connections of the active shield. Thus, the sense coil 32 is connected via the mu metal shield 110 as a close coupled transformer with the driven coil 34, the output of the sense coil being taken through an opamp 33 of high gain. The driven and sense coils form a closely coupled transformer with a stable negative feedback loop including the operational amplifier. The driven coil produces a null output at the sense coil and this is virtually equivalent, i.e., produces a zero sum field through the mu-metal shield. The resistor provides a DC return path in order to establish an operating point in the linear region of the operational amplifier.

CLOCK AND SAMPLING LOGIC

Referring now to FIGS. 1 and 3, the clock circuits 20 and the sampling logic and control circuits consisting of 36, 40, flip-flop 4013-3, 120, and 122 will now be described. The clock consists of a 555-1 multivibrator oscillator which is divided twice in the flip-flops 4013-1, -2, to provide two 10 Hz outputs of opposite phase. These outputs respectively go to valve driver circuits consisting of collector to base coupled transmission amplifiers Q1, Q2 for turning on and off the valves V1, V2 between normally open and normally closed positions. Each of the valves is positively driven from its normally closed to normally open position and returned. The 10 Hz output from the second 4013 divider is also taken to the input of a variable duration one shot multivibrator 555-2 triggered by each transition of the clock. Its purpose is to provide a phase adjustment in order to bring the phase amplitude detector formed by the sample and hold circuits and difference amplifier to be hereinafter described into a phase with the output signal from the detector. The output of the one shot multivibrator 555-2 is delivered to a second one shot multivibrator 555-3 of duration 2/60 seconds to establish the sample time of the sample and hold circuits. One shot 555-3 is triggered by the falling edge of the output from the first multivibrator. The positive transition of the output of one-shot 555-3 is provided as a clock input to a flip-flop 4013-3, the data input of which is taken from the clock. Thus, the output of the flip-flop 4013-3 taken from Q, $\overline{Q}$ applied to the steering logic 120 and then the inventers 122. The output of the flip-flop is triggered into a position which depends on the state of the clock 20. By virtue of the NOR gate arrangement of the NOR gates 120A, 120B and 120C, the respective sample pulse generated by logic element 36 is steered to one or the other of the sample and hold integraters by the logic 40. A second inverting logic 42 is used to drive the hold circuits so that the sample and hold are in one state or the other and positively driven by the logic. Because the signals from the clock are symmetrical, one being one while the other is off and visa versa, it is sufficient to drive the data input of flip-flop 4013-3 with a single one of the clock outputs.

SIGNAL PROCESSING CIRCUITS

Figure 4:
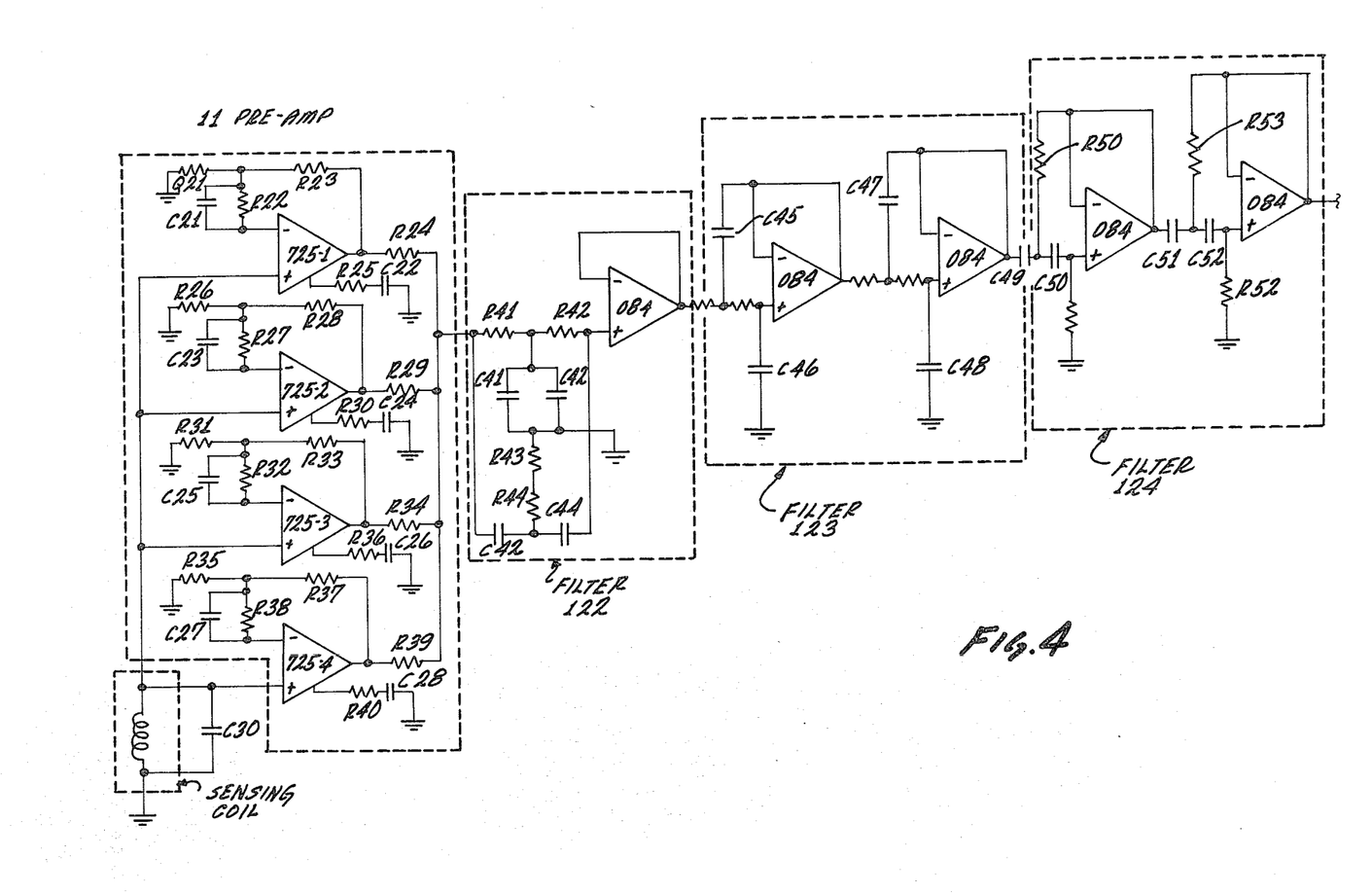

The output of the sense coil from the magnetic sensor is taken through a multiple stage input amplifier which comprises four identical high gain opamp amplifiers 725-1, -2, -3, -4 arranged in a parallel low noise opamp configuration. The outputs of these amplifiers are summed in a single junction and thus averaged so that if N is the number of amplifiers the noise will be $1/\sqrt{N}$ times the noise generated by a single amplifier. This configuration reduces the noise by a factor of 2. The output of the amplifiers is taken through filters 122, 123 and 124. Filter 122 is a 60 cycle notch filter with buffer amplifier. Filter 123 is a 24 dB per octave low pass filter with a roll-off starting at 10 cycles while filter 124 is a 24 dB per octave high pass filter with a roll-off starting also at 10 cycles. Together, the filter and amplification system provides for a deep surpression of 60 cycles signals while providing a selective amplification of 10 cycle signal being generated by the magnetic sensor. A variable amplifier 126 is used to adjust the instrument gain and sensitivity.

SAMPLE, HOLD AND DIFFERENCE AMPLIFYING CIRCUITS

Figure 5:
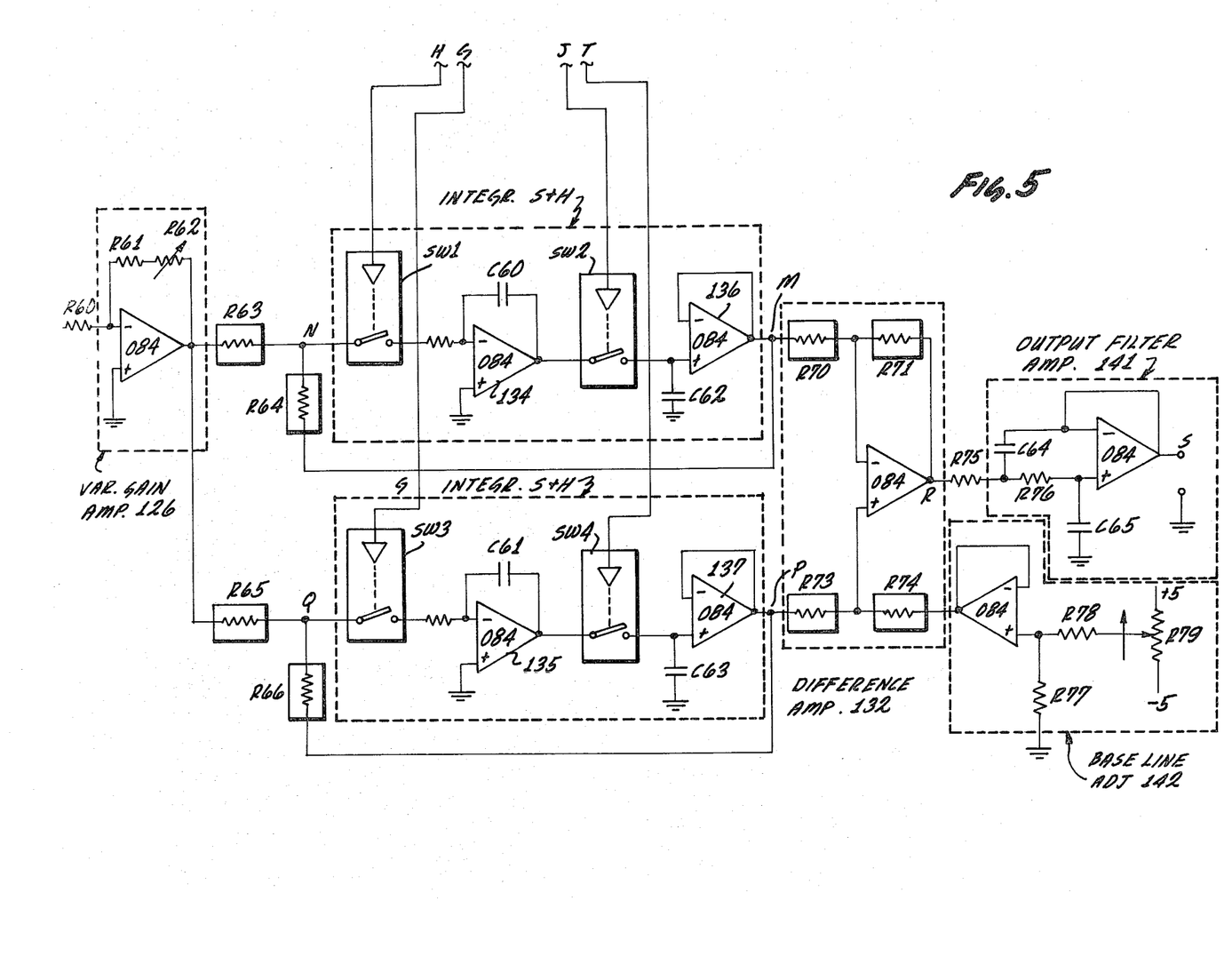

Referring to FIGS. 1 and 5, two sample and hold circuits 131 and 132 are provided for the respective output of the two valve connections and are identical so that the description of one will serve as a description of the other. The sample and hold circuits average the output period over 2 cycles of the line frequency or 2/60ths of a second. Therefore, all signals that are multiples of 30 Hz are rejected by the sample and hold circuits. Each sample and hold circuit consists of a switch SW1, SW3 for opening the signal line in response to a input signal followed by an integrating opamp 134, 135 and a second switch SW2, SW4 followed by a sample and hold amplifier 136, 137. The control input to switches are respectively connected to the outputs of the steering logic and inverters 40 and 42. Thus, it will be seen that the signals G and H as given are connected to operate the sample switches S1 and S3, the input to which are identical signals K=N, Q. The inverter outputs I, J are connected to control switches S2 and S4. Thus, when signal H is energized to close S1 integrater 134 receives signal N and integrates the same for that period. In the meantime, the signal J from the inverter is in opposition and therefore S2 will be open and no signal is received to the input of the hold circuit 137. The opposite condition obtains when the signal is inverted and H is caused to open S1 so that no further signal appears at that integrator. At that time, S2 is closed by the inverted signal J and the previously integrated value is then applied to control the hold circuit 137. The output is summed in the difference amplifier 141 and filtered to remove the steps caused by sampling in filter amplifier 142.

Figure 7:
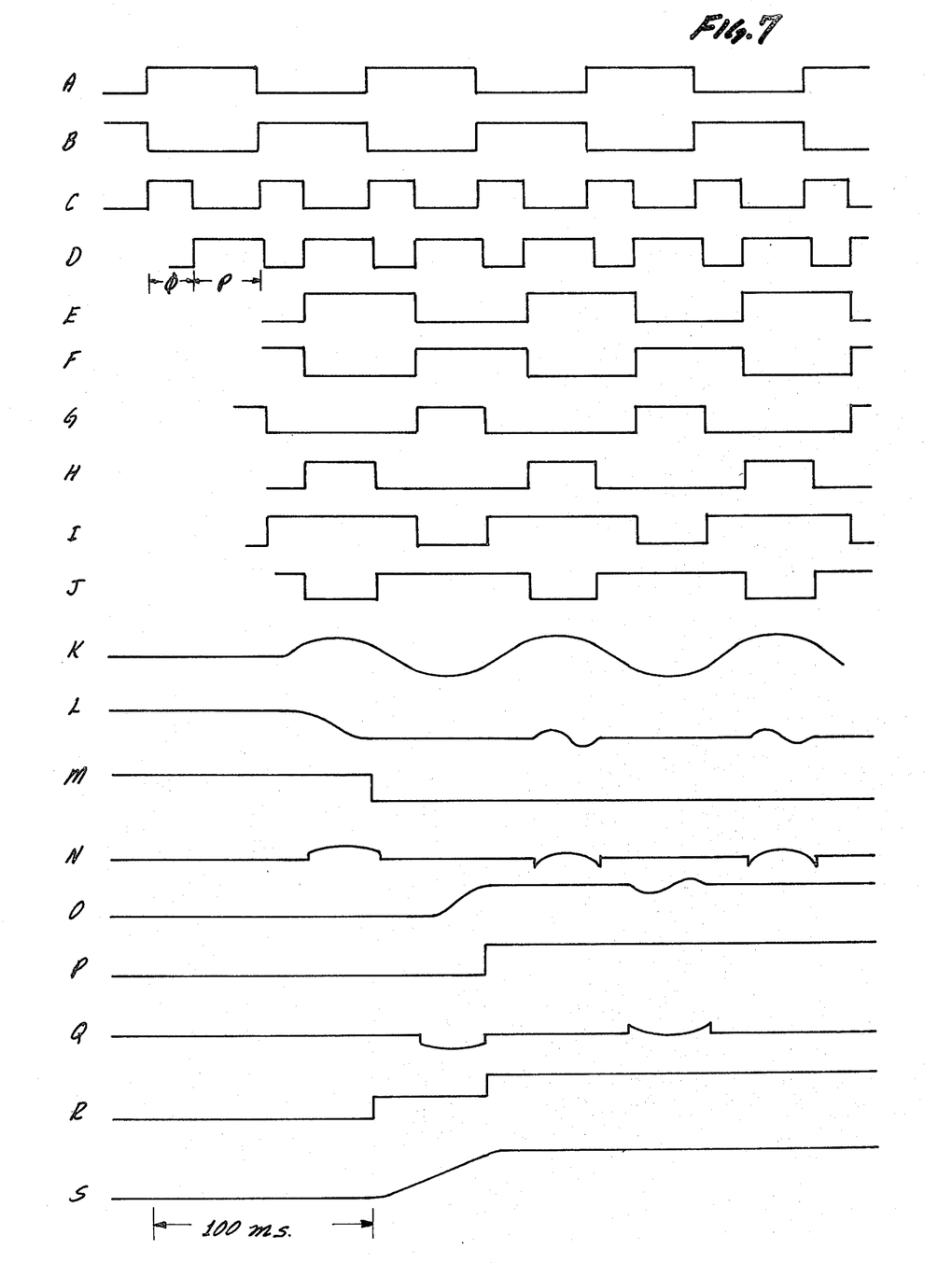
FIGS. 7A–7S are timing diagrams developed in the operation of the oxygen detection systems of FIGS. 1 through 6.
Figure 8A:
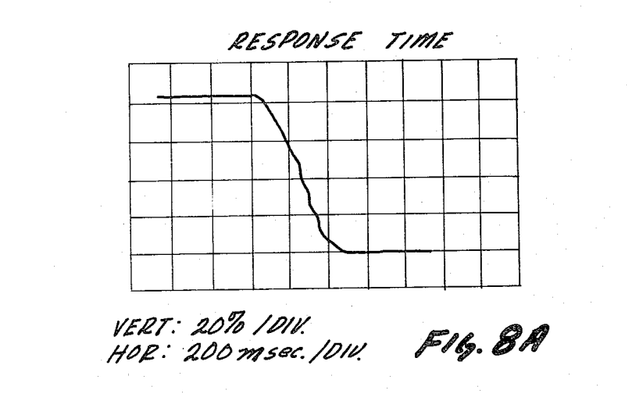
Figure 8B:
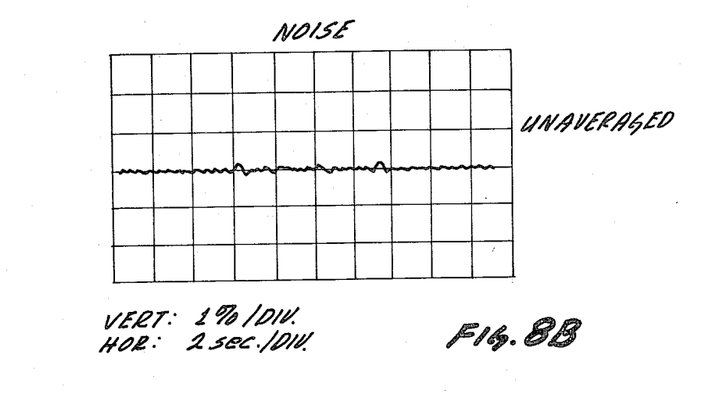
Figure 8C:
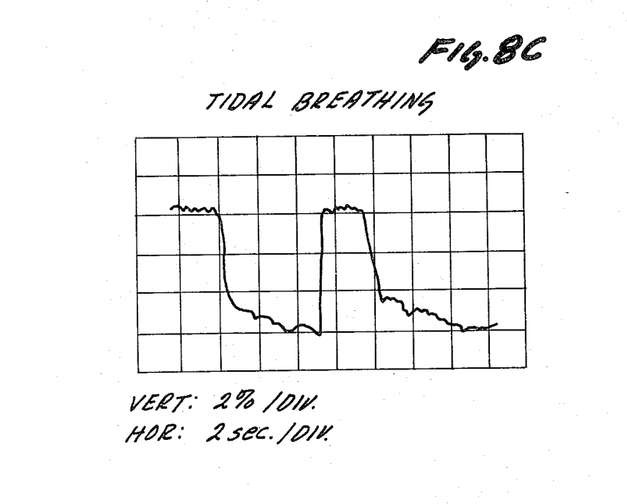
Figure 8D:
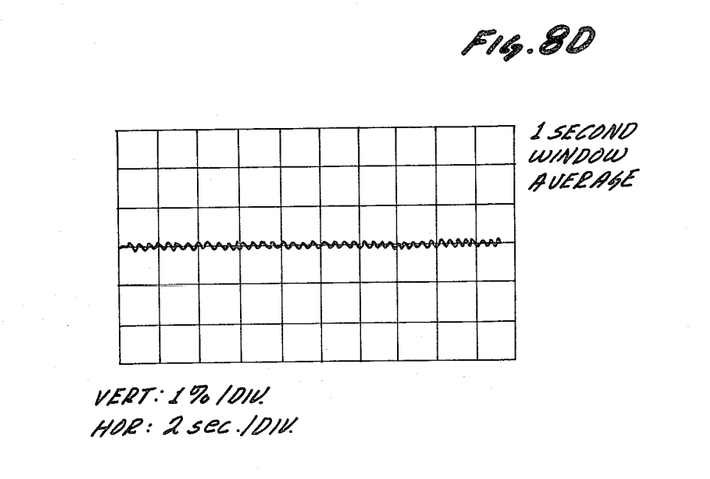

The following is a description of the waveforms of FIGS. 7A relating to the foregoing circuits, the capital letter designations corresponding to those marked on FIGS. 3-6.

A and B are the clock outputs. When A is high, valve V1 is actuated and when B is high, valve V2 is actuated. C is the output of the phase adjusting one-shot and D is a succession of 1/30 sec pulses triggered by the falling edge of C. Note that D is not the complement of C, and that in the past the falling edge of D does not correspond with the rising edge of C. E and F are the outputs of flip-flop 38. Note that E changes to the state of B at each rising edge of D. The complementary outputs E and F are applied to NOR gates along with D inverted. The result is G and H which determine the sampling window for sample circuits 131, 132, respectively. I and J are the complements of G and H.

Assuming there is a condition of no signal followed by a signal (line K), the sampling cycle for sample circuit 131 will be traced. It will be assumed that integrator L and holding circuit M are at zero. During the first one-half cycle of K, H goes high for 2/60 sec, turning on S1. S2 is off, being driven by complementary signal J. The intergrator sees N which is one-half the difference of K and M. Integrator waveform L results. Since S2 is open during integration it holds the value of the last integral. At the end of the integration (i.e., when S1 opens) S2 closes which updates M. The time constant of the integrator is chosen so that the value of M during integration (which is the value of integral L at the start of integration) produces a change in the value of the integral of equal magnitude and opposite sign. The effect is that the difference between the average value of K during integration and output M of 6, is applied to the integrator in a fashion tending to make this difference zero. This is illustrated in the second positive half cycle in which integrated signal N is seen to produce a zero net change in integrator L. Hence output M remains constant. In a similar fashion output F of 7 is produced from negative one-half cycles. Their difference R is the raw unfiltered output, and S is the signal after filtering.

Note that DC error at the output K or L as well as all harmonics of 30 Hz (which includes all harmonics of 60 Hz) have no effect on the output of the difference amplifier. The former disappear in the difference amplifier and the latter always sum to zero in the integrators.

The use of such a sophisticated phase and amplitude detector is made necessary by the need to reject sizeable random and 60 Hz related noise. Similar features would result from the use of a 4 quadrant multiplier in which the sigal K were multiplied with a fixed reference sine wave which was synchronous with valve action. However, such circuits do not exhibit the high stability and low offset of the circuit described.

FIGS. 8 are oscillograms showing performance curves for an instrument built according to the present invention. Measurement is at sea level pressure. To convert to PO2, multiply vertical reading in percent by 760 mm Hg and divide by 100.

I claim:

1. In a system for measuring the percentage content of oxygen gas in an unknown or sample gas by comparison with a reference gas, the combination of a magnetic bridge including means forming a pair of major flux circuits, each having a gap therein, valve means for synchronously and alternately filling said gaps with the reference and sample gases, means interconnected between said major flux circuits for forming a null magnetic bridge arm for deriving a magnetic flux proportional to the difference in circuit reluctance of the major magnetic circuits, sense coil means coupled to said null arm for generating a time varying electrical signal proportional to the magnetic flux in said null arm.

2. An oxygen detector as in claim 1 in which said valve means comprises valves arranged for being connected to each of the magnetic gaps in said major flux carrying magnetic circuits, clock means for synchronously driving said valves, means for developing a synchronous sampling signal from said clock means, sample and hold circuit means for sampling and integrating of the respective signals from the sense coil during the periods when the difference in magnetic reluctance of the major paths is due to subtraction from the reference and visa versa, and further including means coupled to said sense coil for subtracting said integrated signals from each other to derive an electrical signal proportional to twice the magnetic susceptibility difference of said gases.

3. The oxygen detection system as in claim 1 further in which said major magnetic circuits include means forming an annular sample and reference gas chambers including a gap defining peripheral ring manifold, a field shaping ring means defining an annular gap between the bridge arm, the source magnet and the gap defining annual ring manifold said field rings being positioned on each side thereof to complete said gap and to support the remaining members, said rings being of low permeability.

4. A oxygen detection system as in claim 1 further including an active shield means surrounding said magnetic sensor and including coil means for sensing stray fields therein, driven coil means for generating a null field in response to said sensed stray fields and an amplifier for receiving the output of said sensing coil and for amplifying the same and driving said null field driven coil.

5. In a magnetic bridge circuit in which a null arm connects primary flux paths and serves as a magnetic bridge to sense differences in said primary paths, an active shield for surpressing stray induced magnetic fields comprising a sense coil surrounding said null bridge arm, a driven null coil surrounding said null arm and closely coupled with said sense coil to form a closely coupled transformer, an amplifier having an input connected to said sense coil and an output connected to drive said driven coil to produce a magnetic field in opposition to a sensed stray EM fields crossing said sense coil.

6. A magnetic bridge active shield as in claim 5 further including a mu metal shield associated with said sense and driven coils.

7. An active shield as in claim 6 in which said sense coil, driven coil and mu metal shield are in the form of cylindrical shell of right cylindrical cross-section.

* * * * *